(12) United States Patent
Berchtold

(10) Patent No.: US 6,374,621 B1
(45) Date of Patent: Apr. 23, 2002

(54) REFRIGERATION SYSTEM WITH A SCROLL COMPRESSOR

(75) Inventor: Eric D. Berchtold, Loveland, OH (US)

(73) Assignee: Cincinnati Sub-Zero Products, Inc., Cincinnati, OH (US)

( * ) Notice: Subject to any disclaimer, the term of this patent is extended or adjusted under 35 U.S.C. 154(b) by 0 days.

(21) Appl. No.: 09/644,505

(22) Filed: Aug. 24, 2000

(51) Int. Cl.[7] ............................................... F25B 41/00
(52) U.S. Cl. ....................................................... 62/114
(58) Field of Search .................................. 62/498, 114

(56) References Cited

U.S. PATENT DOCUMENTS

| | | |
|---|---|---|
| 4,550,574 A | 11/1985 | Hohman |
| 4,683,424 A | 7/1987 | Cutright et al. |
| 4,788,829 A | 12/1988 | Takemasa et al. |
| 4,949,031 A | 8/1990 | Szasz et al. |
| 5,102,316 A | 4/1992 | Caillat et al. |
| 5,341,654 A | 8/1994 | Hewette et al. |
| 5,342,183 A | 8/1994 | Radfalovich et al. |
| 5,342,184 A | 8/1994 | Comparin et al. |
| 5,342,185 A | 8/1994 | Anderson |
| 5,358,391 A | 10/1994 | Wallis et al. |
| 5,370,513 A | 12/1994 | Fain |
| 5,372,490 A | 12/1994 | Fain |
| 5,397,998 A | 3/1995 | Soeno et al. |
| 5,440,894 A * | 8/1995 | Scaeffer et al. ................ 62/203 |
| 5,545,019 A | 8/1996 | Beck et al. |
| 5,806,336 A | 9/1998 | Sunaga et al. |
| 5,916,252 A * | 6/1999 | Yoshida et al. ................ 62/204 |
| 5,929,340 A | 7/1999 | Cochran et al. |
| 6,005,404 A | 12/1999 | Cochran et al. |
| 6,017,205 A | 1/2000 | Weatherston et al. |
| 6,023,935 A | 2/2000 | Okazaki et al. |
| 6,047,557 A * | 4/2000 | Pham et al. ................ 62/228.5 |

* cited by examiner

Primary Examiner—William Doerrler
Assistant Examiner—Malik N. Drake
(74) Attorney, Agent, or Firm—Charles R. Wilson

(57) ABSTRACT

A refrigeration system includes a singular scroll compressor, a condenser and a compressor. The system is charged with R410A refrigerant. The system finds particular use in an environment testing and conditioning apparatus having means to deliver conditioned air efficiently to a test chamber. The apparatus comprises the test chamber and an air plenum chamber.

9 Claims, 3 Drawing Sheets

REFRIGERATION SYSTEM WITH A SCROLL COMPRESSOR

This invention relates to a refrigeration system. More particularly, it relates to a refrigeration system based on a scroll compressor to efficiently provide a flow of air having a reduced temperature.

Refrigeration systems are used in different settings to lower the temperature of a substance below that of its surroundings. They are very commonly used in residential, commercial and industrial plant air conditioning systems where air temperature is controlled. They are also used in specialized situations such as the chemical processing industry for removing heat of chemical reactions, liquefying process gasses and numerous other materials processing steps where air, liquid and solid temperatures must be regulated. Regardless of end use, all refrigeration systems include a compressor, a condenser and an evaporator. All include a refrigerant circulating throughout the system. Different temperature limits and temperature reducing capacities are attained depending on the system components and refrigerant selected.

Environment testing apparatuses in particular are used by many manufacturers in an attempt to predict a product's durability. A product can be subjected to very controlled temperatures and humidities. In certain instances, a short testing period at preselected conditions will adequately test the product. Oftentimes, the testing is conducted at environmental extremes to hasten the testing process. In effect, a meaningful prediction of a product's long term durability can be achieved in a relatively short time span.

Environment conditioning apparatuses are also used by manufacturers to subject products to controlled conditions, such as temperature, humidity and pressure. The conditioning is a part of the manufacturing process and is used to impart a certain quality to the product.

Apparatuses built for the environment testing uses discussed above typically include a housing with a test or conditioning chamber for holding the product and a plenum chamber for supplying conditioned air to the test chamber. When reduced temperatures are called for, the conventional refrigeration system of a compressor, condenser and evaporator are connected and placed in communication with the plenum chamber. In such systems, the evaporator is mounted in the test chamber or in an air plenum chamber which is in fluid communication with the test chamber. A cooled refrigerant flowing through coils in the evaporator removes heat from the chamber and thus lowers the chamber temperature. The cooled refrigerant supplied to the evaporator also flows in a closed loop through the compressor and the condenser. The refrigerant is thus continuously cycled in a vapor-compression refrigeration cycle. When an elevated temperature is required, a heater system is in communication with the plenum chamber. Some apparatuses include both refrigeration and heater systems.

Both testing and conditioning apparatuses desirably operate as efficiently as possible. This is particularly important with certain apparatuses designed for use where temperatures substantially below room temperature are required. Efficiency of operation can come from the apparatus itself as well as the refrigerant being used. Various capacity compressors, condensers (air cooled or water cooled) and evaporators of varying designs are available. Refrigerants with different physical characteristics such as boiling points are also known and commercially available. The particular refrigerant selected is typically based on its chemical properties, thermodynamic properties, physical properties, and safety considerations. The refrigerant in effect is matched with the system capacity and the desired test chamber temperature.

Cascade refrigeration systems are known and commonly believed necessary to reach substantially reduced temperatures in the test chamber of a testing and conditioning apparatus. In the cascade refrigeration system, a first stage system including a compressor and condenser cools a refrigerant. This cooled refrigerant is then passed in a heat-exchange relationship with a refrigerant of the second stage. The temperature of this second stage refrigerant is thus lowered before the refrigerant passes through coils in an evaporator. The evaporator is positioned in the test chamber or is in fluid communication with the test chamber. Such basic cascade refrigeration systems have been further modified with bypass circuits to enhance operating efficiencies.

The cascade refrigeration systems are very effective for providing a substantially reduced temperature in the test chamber of an environment testing and conditioning apparatus. However, the need for two compressors in particular substantially increases the unit's initial cost. The cost of operating and maintaining the system is also noticeably higher. Increased personnel training to properly set-up and run the apparatus also adds to the cost of operation and increases the chance for operator error.

There is an ongoing need for less costly and more efficiently operated refrigeration systems. In accord with this need, there has now been developed a system which is capable of supplying substantially reduced temperatures using only a singular compressor. The system is ideally used as part of a testing and conditioning apparatus to maintain temperature within a test chamber in a narrow reduced temperature range in a cost effective manner.

SUMMARY OF THE INVENTION

A refrigeration system includes a singular scroll compressor, a condenser and an evaporator operatively connected together. The refrigeration system is further charged with R410A refrigerant. The scroll compressor and R410A refrigerant synergistically provide very efficient cooling to a reduced temperature of at least about −35 degrees F. The system finds widespread use. In particular, an environment testing and conditioning apparatus which comprises a housing having a test chamber, an air plenum chamber and a mechanics chamber utilizes the refrigeration system. The apparatus is very cost effective because of a need for only the singular scroll compressor and the efficient running of the refrigeration system.

DETAILED DESCRIPTION OF THE INVENTION

The refrigeration system of the invention is described in the following paragraphs and with reference to the drawings. The system has many applications, particularly in commercial and industrial settings. One ideally suited application is as part of an environment testing and conditioning apparatus and, for this reason, is described in detail. It should be understood the refrigeration system of the invention is useful wherever an efficient refrigeration system capable of attaining a reduced air temperature is needed. In accord with this invention, the refrigeration system is particularly useful for efficiently maintaining an air temperature in a chamber of at least about −35 degrees F. and preferably from about −40 degrees F. to about −50 degrees F.

Figure 1:
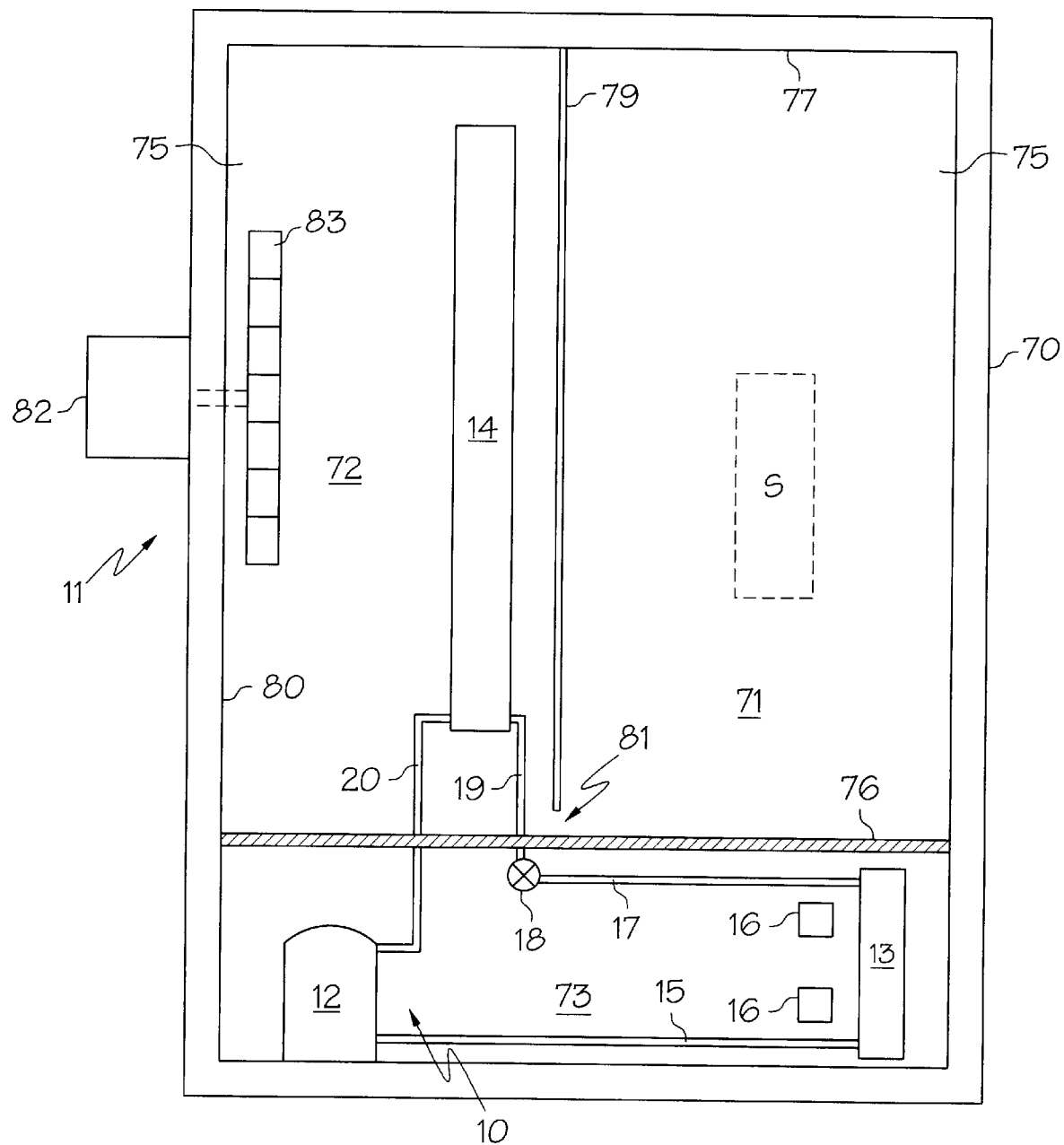
FIG. 1 is a side elevational view of the refrigeration system of the invention as part of an environment testing and conditioning apparatus partially cut-away to show the circulation of air within the apparatus.
Figure 3:
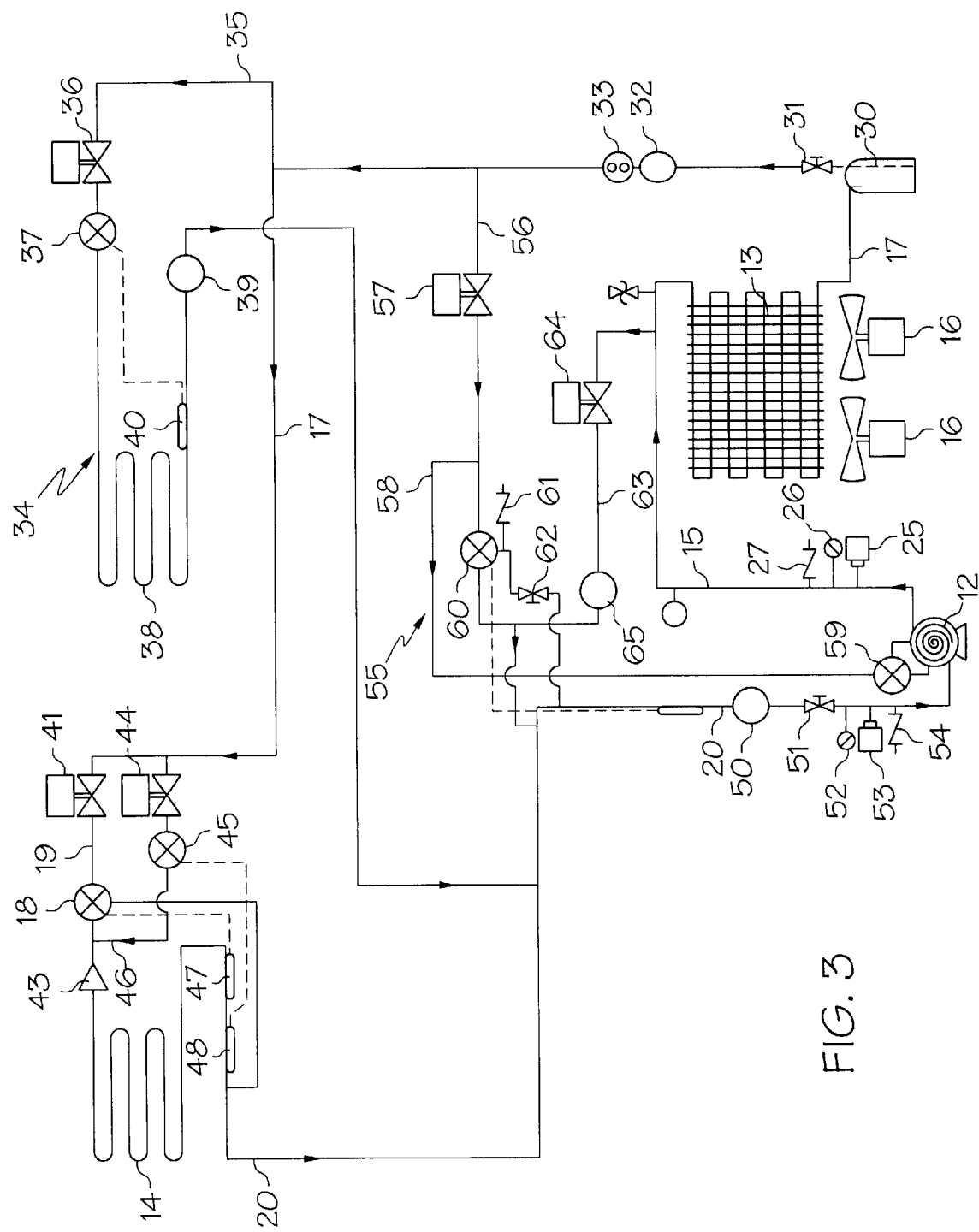
FIG. 3 is a schematic diagram of the refrigeration system used in the environment testing and conditioning apparatus of FIG. 1.

FIG. 1 depicts the refrigeration system 10 of the invention in general block form as part of the environment testing and conditioning apparatus 11. FIG. 3 depicts the refrigeration system in schematic form and includes controls used in its operation. The refrigeration system 10 includes a scroll compressor 12, a condenser 13 and an evaporator 14. In accord with the invention, the system is charged with a R410A refrigerant. The system and its operation are described in more detail in the following paragraphs.

Scroll compressors as used in the invention are commercially available from the Copeland Corporation. While known for a number of years, their popularity in refrigeration systems has increased in recent years. The scroll compressor 12 is constructed of two scroll members, each having an end plate and a spiral wrap. Typically, one scroll member is fixed in position and the other orbits during use. The scroll members are arranged in an opposing manner so that the scroll members are interfitted. They are mounted in a housing so that one scroll member moves orbitally with respect to the other scroll member. During this orbiting movement, the spiral wraps define moving gas pockets which decrease in size as they progress radially inwardly from an outer position at relatively low suction pressure to a central position at relatively high discharge pressure. The refrigerant gas in the compressor is compressed as it moves inwardly and the volume of compression space decreases. The refrigerant gas exiting from the compressor is in a superheated vaporous form.

Still with reference to FIG. 1, the refrigerant, in the vaporous form, exiting from the outlet of the scroll compressor 12 passes through a pipeline 15 to the condenser 13. The condenser 13 is used to cool the refrigerant sufficiently that it changes to a liquid form. Numerous condenser designs are available. As shown, the condenser has coil tubing through which the refrigerant passes and further is air cooled. Two fans 16 are positioned adjacent the condenser 13 to provide ambient air cooling, preferably below about 90 degrees F. The condenser 13 can also be water cooled in known fashion. Other condensers, for example tube and shell condensers can be used.

The refrigerant exiting the condenser 13 is in a liquid form. It passes through a pipeline 17, an expansion valve 18, a pipeline 19 and into the evaporator 14, still in a liquid form. The evaporator 14 is a finned coil evaporator. It includes a series of tubes through which the refrigerant passes. A set of flat fins mounted on the tubes are used to transfer heat from the surrounds to the refrigerant within the tubes. Other known evaporators of varying designs can be used. The refrigerant in the tubes is vaporized during a heat extraction process. As evident in FIG. 1, the refrigerant now passes back through a pipeline 20 to the scroll compressor 12 to begin the refrigeration cycle again.

In accord with this invention, the aforediscussed refrigeration system is initially charged with the R410A refrigerant. The R410A refrigerant is a mixture of 50% by weight of difluoromethane ($CH_2F_2$) and 50% by weight of difluorotrifluoroethane ($CHF_2CF_3$). It is commercially available from several sources. The use of the R410A refrigerant in a refrigeration system utilizing a scroll compressor results in unexpected BTU capacity and evaporating temperature to the extent that the use of a singular scroll compressor gives the desired reduced air temperature. The table which follows compares the R410A refrigerant with a R404A refrigerant in the same refrigeration system comprising the singular scroll compressor, condenser and evaporator.

Capacity (BTU/hr) at Condensing Temperature of 90 Degrees F.

| Evaporating Temperature (degrees F.): | −15 | −20 | −25 | −30 | −35 | −40 | −45 | −50 | −55 | −60 | −65 | −70 |
|---|---|---|---|---|---|---|---|---|---|---|---|---|
| R404A | 16200 | 14400 | 12800 | 11400 | 10050 | 8870 | — | — | — | — | — | — |
| R410A | 16700 | 16349 | 15000 | 13560 | 12000 | 10152 | 8308 | 7369 | 6500 | 5087 | 4260 | 3434 |

As evident from the table, the refrigeration system using the R410A refrigerant has more capacity, up to an evaporating temperature of −15 degrees F. As a result, the refrigeration system of the invention can supply a defined cooling temperature air more efficiently since the system runs less, i.e. operating costs are less and equipment usage is less. A conventional cascade refrigeration system with the R404A refrigerant is able to attain the comparable capacity, though it is substantially more costly because of the extra equipment needed. The system of the invention is also able to efficiently reach much lower evaporator temperatures than the refrigeration system using the R404A.

Reference is now made to FIG. 3 for a more detailed description of operation of the refrigeration system 10, including the controls used in the system. As depicted, the scroll compressor 12 has the pipeline 15 in fluid communication with the condenser 13. A switch 25, a high pressure gauge 26 and a service port 27 are provided in the pipeline 15. Refrigerant leaving the compressor 12 is in a hot gaseous form. As the refrigerant passes through the pipeline 15 and into the condenser 13, it is transformed into a liquid form. The fans 16 are used to air cool the condenser 13. The liquid refrigerant now passes through the pipeline 17 and into a receive 30. From there, it continues through the pipeline 17 to a valve 31 and into a filter drier 32. A liquid indicator 33 is interposed in the pipeline 17. The liquid refrigerant can continue its flow through the pipeline 17 directly to the expansion valve 18 and then through the pipeline 19 to the evaporator 14. 10

As shown in FIG. 3, an optional humidity control system depicted generally as 34 is interposed in the pipeline 17 prior to the evaporator 14. It is accessed by a bypass line 35. The humidity control system includes a wet coil solenoid 36, a wet coil valve 37, a wet coil evaporator 38 and a valve 39. A sensor 40 is connected to the wet coil valve 37. Activation of the humidity control system 34 is optional, dependent only on the particular use of the refrigeration system 10 and operating conditions needed. When the optional humidity control system is provided, a primary solenoid 41 and a distributor 43 are provided as is a secondary solenoid 44, valve 45 and a bypass line 46. Prior to reaching the evaporator 14, the liquid refrigerant in the pipeline 17 passes through the solenoid 41, the expansion valve 18 and the distributor 43. It then passes into the pipeline 19, the evaporator 14 and exits through the pipeline 20. Temperature sensors 47 and 48 in the pipeline 20 are in communication with the valves 18 and 45, respectively. The refrigerant in the evaporator 14 changes to a gas and in the process absorbs heat from its surrounds. The refrigerant now flows back through the pipeline 20 to the scroll compressor 12. A workcase pressure regulator 50, a service valve 51, a low pressure gauge 52, a switch 53 and a service port 54 are interposed in the pipeline 20 before reaching the scroll compressor 12.

An evaporator bypass system shown generally as 55 is used to enhance efficiency of the refrigeration system 10. It is activated when a desired operational air temperature is reached, thereby allowing the compressor 12 to run continuously. The system 55 includes a bypass pipeline 56, a solenoid 57, a pipeline 58 leading back to the compressor 12 and a thermostatic expansion valve 59. The system 55 further comprises a liquid injection valve body 60 with a service port 61 and an isolation valve 62. A pipeline 63 leading to the valve body 60 includes a hot gas bypass solenoid 64 and a hot gas regulator 65.

The preferred use for the refrigeration system 10 is as an integral part of the environment testing and conditioning apparatus 11 of the invention. As described and shown in FIGS. 1 and 2, the apparatus 11 has a structural lay-out which is ideally suited for the product sample being tested. It should be understood that other apparatus structural lay-outs are feasible, as well as different physical parameters to accommodate all sizes and numbers of product for testing and conditioning. The apparatus 11 comprises a cabinet 70 having a test chamber 71, an air plenum chamber 72, and a mechanics chamber 73. The testing and conditioning apparatus 11 also has operably associated with it the refrigeration system shown generally as 10 as described in detail above with associated controls for precisely regulating the temperature and optionally humidity within the test chamber 71. The components of the refrigeration system 10 are structurally a part of the test apparatus 11, though are not shown in detail. One or more of the components can as well be external of the apparatus, though preferably are a structural part of it for reasons of compactness and ease of operation.

Figure 2:
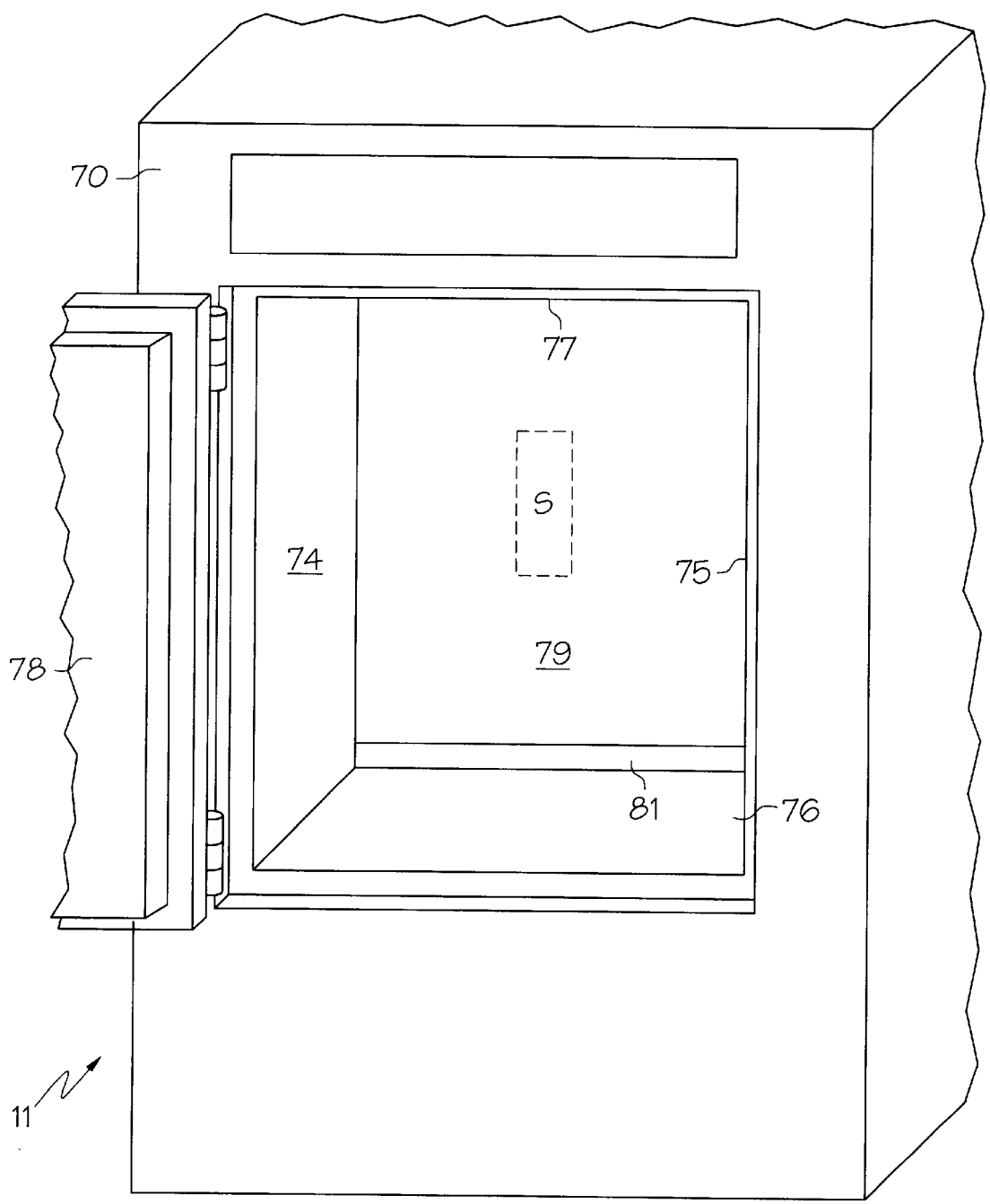
FIG. 2 is a front elevational view of the environment testing and conditioning apparatus of FIG. 1 wherein an access door has been opened to show a test chamber.

As best seen in FIG. 2, the test chamber 71 of the testing apparatus 11 is defined by solid insulated panels serving as side walls 74 and 75, floor 76, ceiling 77, and a door 78 by which access is gained to the chamber's interior. A flat perforated interior wall 79 completes the test chamber 71. A single product sample is shown in phantom in FIGS. 1 and 2. The test chamber is used for testing the single product sample or several samples if desired. Conventional mounting means are used to hold the product sample within the test chamber, preferably in a suspended state. A rack with product clamps is one convenient means for this purpose.

Now with reference to FIG. 1, the air plenum chamber 72 is disposed in the cabinet 70 directly behind the test chamber 71. It is defined by the opposed side walls 74 and 75, floor 76, ceiling 77, flat perforated interior wall 79 and a back wall 80. It houses a part of the refrigeration system and is a part of the reduced temperature air flow path. The air plenum chamber 72 is in communication with the test chamber 71 through a slot opening 81 located between the lower terminal edge of the flat perforated interior wall 79 and the floor 76 of the chambers. The mechanics chamber 73 is located under the floor 76 of the cabinet's test and air plenum chambers.

As shown in FIG. 1 by air flow directional arrows, conditioned air is forced to flow from the air plenum chamber 72, through the flat perforated interior wall 79 and into the test chamber 71. It then flows from the test chamber 71 through the slot opening 81 and back into the air plenum chamber 72. A blower with its motor 82 mounted on the outside of the cabinet 70 and a fan wheel 83 positioned within the air plenum chamber 72 forces the air to move in the direction indicated.

The flat perforated interior wall 79 partly defining the test chamber 71 also aids in creating a desired uniform air flow velocity. It is substantially vertically disposed and free standing such that all the air flowing from the air plenum chamber 72 passes through it and into the test chamber 71. The hole density and the hole number, diameter and depth parameters in the flat perforated side wall can be varied as needed.

In operation, a product sample is mounted in the test chamber of the testing and conditioning apparatus and the door closed. The apparatus' cooling unit and optional humidity unit are activated and air is circulated through the air plenum and test chambers. As sufficient pressure has been created in the air plenum chamber, air is forced into the test chamber and ultimately drawn back into the air plenum chamber. The air which contacts the sample product has a preselected temperature and humidity and is flowing at a substantially uniform velocity throughout the upstream side of the test chamber.

As should be apparent from the above description of the invention, the refrigeration system of the invention efficiently provides a reduced air temperature. It is ideally used to provide an air temperature of at least about −35 degrees F. and preferably about −40 degrees F. to about −50 degrees F. The system is cost effective initially because of the need for only a singular scroll compressor. The system is also cost effective during operation because of reduced power needs required of the scroll compressor and less operating time. The scroll compressor and R410A refrigerant unexpectantly and synergistically operate to contribute to the efficiency of the system. This efficiency is achieved over a wide horsepower range of scroll compressors.

Having described the invention in its preferred embodiment, it should be clear that modifications can be made without departing from the spirit of the invention. It is not intended that the words used to describe the invention nor the drawings illustrating the same be limiting on the invention. It is intended that the invention only be limited by the scope of the appended claims.

I claim:

1. A refrigeration system for efficiently providing cooled air, said system comprising (i) a singular scroll compressor, (ii) a condenser, and (iii) an evaporator operatively connected and further wherein the system is charged with R410A refrigerant for efficiently providing air having a reduced temperature of at least about −35 degrees F.

2. The refrigeration system of claim 1 wherein the condenser is air cooled.

3. The refrigeration system of claim 1 wherein the condenser is water cooled.

4. The refrigeration system of claim 1 wherein the system efficiently provides air cooled to a temperature of from about −40 degrees F. to about −50 degrees F.

5. An environment testing and conditioning apparatus wherein products are exposed to a reduced temperature in an efficient manner, said apparatus comprising:
   (a) a cabinet having a test chamber and an air plenum chamber; and
   (b) a refrigeration system operably associated with the cabinet for delivering cooled air to the test chamber, said refrigeration system including (i) a singular scroll compressor, (ii) a condenser, and (iii) an evaporator connected together and further wherein the system is charged with R410A refrigerant for maintaining the test chamber at a substantially constant reduced temperature of at least about −35 degrees F.

6. The environment testing and conditioning apparatus of claim 5 wherein the condenser of the refrigeration system is air cooled.

7. The environment testing and conditioning apparatus of claim 5 wherein the condenser of the refrigeration system is water cooled.

8. The environment testing and conditioning apparatus of claim 5 wherein the refrigeration system efficiently provides air cooled to from about −40 degrees F. to about −50 degrees F. to the test chamber.

9. An environment testing and conditioning apparatus wherein products are exposed to a reduced temperature in an efficient manner, said apparatus comprising:
   (a) a cabinet having a test chamber and an air plenum chamber; and
   (b) a refrigeration system operably associated with the cabinet for delivering cooled air to the test chamber, said refrigeration system including (i) a singular scroll compressor, (ii) an air cooled condenser, and (iii) an evaporator operably connected together and further wherein the system is charged with R410A refrigerant for efficiently maintaining the test chamber at a substantially constant reduced temperature of from about −40 degrees F. to about −50 degrees F.

* * * * *